United States Patent
Halstead et al.

(10) Patent No.: US 10,350,382 B1
(45) Date of Patent: Jul. 16, 2019

(54) HIGH TORQUE CATHETER AND METHODS OF MANUFACTURE

(71) Applicants: Greg Halstead, Sunnyvale, CA (US); Michael P. Allen, Los Altos, CA (US)

(72) Inventors: Greg Halstead, Sunnyvale, CA (US); Michael P. Allen, Los Altos, CA (US)

(73) Assignee: Embolx, Inc., Sunnyvale, CA (US)

( * ) Notice: Subject to any disclaimer, the term of this patent is extended or adjusted under 35 U.S.C. 154(b) by 0 days.

(21) Appl. No.: 16/004,247

(22) Filed: Jun. 8, 2018

(51) Int. Cl.
*A61M 25/00* (2006.01)

(52) U.S. Cl.
CPC ...... *A61M 25/0045* (2013.01); *A61M 25/005* (2013.01); *A61M 25/0012* (2013.01); *A61M 25/0054* (2013.01); A61M 2025/0004 (2013.01)

(58) Field of Classification Search
CPC .......... A61M 25/0045; A61M 25/0012; A61M 25/005; A61M 25/0054; A61M 2025/0004
See application file for complete search history.

(56) References Cited

U.S. PATENT DOCUMENTS

| | | |
|---|---|---|
| 4,581,017 A | 4/1986 | Sahota |
| 4,737,153 A | 4/1988 | Shimamura et al. |
| 4,748,982 A | 6/1988 | Horzewski et al. |
| 4,892,519 A | 1/1990 | Songer et al. |
| 4,896,669 A | 1/1990 | Bhate et al. |
| 4,909,252 A | 3/1990 | Goldberger |
| 4,944,745 A | 7/1990 | Sogard et al. |
| 4,976,690 A | 12/1990 | Solar et al. |
| 4,990,143 A | 2/1991 | Sheridan |
| 5,000,734 A | 3/1991 | Boussignac et al. |
| 5,040,548 A | 8/1991 | Yock |
| 5,047,045 A | 9/1991 | Arney et al. |
| 5,078,685 A | 1/1992 | Colliver |
| 5,090,958 A | 2/1992 | Sahota |
| 5,137,513 A | 8/1992 | Mcinnes et al. |
| 5,156,594 A | 10/1992 | Keith et al. |
| 5,217,434 A | 6/1993 | Arney |
| 5,279,562 A | 1/1994 | Sirhan et al. |
| 5,334,154 A | 8/1994 | Samson et al. |
| 5,342,386 A | 8/1994 | Trotta |

(Continued)

FOREIGN PATENT DOCUMENTS

| | | |
|---|---|---|
| CN | 101400400 A | 4/2009 |
| CN | 102802698 A | 11/2012 |

(Continued)

OTHER PUBLICATIONS

Halstead et al.; U.S. Appl. No. 16/047,922 entitled "Shaped catheter tip for tracking over a guidewire through turns in the vasculature," filed Jul. 27, 2018**.

(Continued)

*Primary Examiner* — Imani N Hayman
(74) *Attorney, Agent, or Firm* — Shay Glenn LLP

(57) ABSTRACT

A high torque vascular catheter system includes an inner catheter, a proximal outer catheter section, a distal outer catheter section, at least one discrete connection point connecting the inner catheter to the proximal outer catheter section, and at least one discrete connection point connecting the inner catheter to the distal outer catheter section. The distal outer catheter section is more flexible than the proximal outer catheter section. Methods of construction and use of the catheter system are also disclosed.

18 Claims, 5 Drawing Sheets

(56) References Cited

U.S. PATENT DOCUMENTS

| | | | |
|---|---|---|---|
| 5,356,388 A | 10/1994 | Sepetka et al. |
| 5,370,655 A | 12/1994 | Burns |
| 5,423,754 A | 6/1995 | Cornelius et al. |
| 5,423,829 A | 6/1995 | Pham et al. |
| 5,429,605 A | 7/1995 | Richling |
| 5,454,795 A | 10/1995 | Samson |
| 5,470,314 A | 11/1995 | Walinsky |
| 5,484,409 A | 1/1996 | Atkinson et al. |
| 5,498,251 A | 3/1996 | Dalton |
| 5,501,667 A | 3/1996 | Verduin |
| 5,509,910 A | 4/1996 | Lunn |
| 5,556,383 A | 9/1996 | Wang et al. |
| 5,582,619 A | 12/1996 | Ken |
| 5,588,442 A | 12/1996 | Scovil et al. |
| 5,599,326 A | 2/1997 | Carter |
| 5,624,449 A | 4/1997 | Pham et al. |
| 5,643,254 A | 7/1997 | Scheldrup et al. |
| 5,647,198 A | 7/1997 | Mihailovic |
| 5,649,949 A | 7/1997 | Wallace et al. |
| 5,669,905 A | 9/1997 | Scheldrup et al. |
| 5,674,198 A | 10/1997 | Leone |
| 5,690,666 A | 11/1997 | Berenstein et al. |
| 5,690,667 A | 11/1997 | Gia |
| 5,718,711 A | 2/1998 | Berenstein et al. |
| 5,722,424 A | 3/1998 | Engelson |
| 5,749,837 A | 5/1998 | Palermo et al. |
| 5,766,192 A | 6/1998 | Zacca |
| 5,769,830 A | 6/1998 | Parker |
| 5,792,300 A | 8/1998 | Inderbitzen et al. |
| 5,797,874 A | 8/1998 | Spears |
| 5,800,454 A | 9/1998 | Jacobsen et al. |
| 5,807,355 A | 9/1998 | Ramzipoor et al. |
| 5,830,182 A | 11/1998 | Wang et al. |
| 5,833,705 A | 11/1998 | Ken et al. |
| 5,843,032 A | 12/1998 | Kastenhofer |
| 5,843,050 A | 12/1998 | Jones et al. |
| 5,851,203 A | 12/1998 | Van Muiden |
| 5,853,418 A | 12/1998 | Ken et al. |
| 5,891,128 A | 4/1999 | Gia et al. |
| 5,911,717 A | 6/1999 | Jacobsen et al. |
| 5,951,539 A | 9/1999 | Nita et al. |
| 5,951,929 A | 9/1999 | Wilson |
| 5,984,878 A | 11/1999 | Engelson |
| 5,984,929 A | 11/1999 | Bashiri et al. |
| 6,013,084 A | 1/2000 | Ken et al. |
| 6,014,919 A | 1/2000 | Jacobsen et al. |
| 6,019,757 A | 2/2000 | Scheldrup |
| 6,022,340 A | 2/2000 | Sepetka et al. |
| 6,036,670 A | 3/2000 | Wijeratne et al. |
| 6,066,157 A | 5/2000 | Barbere |
| 6,071,286 A | 6/2000 | Mawad |
| 6,090,099 A | 7/2000 | Samson et al. |
| 6,123,714 A | 9/2000 | Gia et al. |
| 6,156,061 A | 12/2000 | Wallace et al. |
| 6,165,163 A | 12/2000 | Chien et al. |
| 6,187,027 B1 | 2/2001 | Mariant et al. |
| 6,190,358 B1 | 2/2001 | Fitzmaurice et al. |
| 6,203,547 B1 | 3/2001 | Nguyen et al. |
| 6,258,080 B1 | 7/2001 | Samson |
| 6,270,495 B1 | 8/2001 | Palermo |
| 6,280,457 B1 | 8/2001 | Wallace et al. |
| 6,287,301 B1 | 9/2001 | Thompson et al. |
| 6,319,228 B1 | 11/2001 | Kastenhofer |
| 6,344,041 B1 | 2/2002 | Kupiecki et al. |
| 6,397,850 B1 | 6/2002 | Scheldrup et al. |
| 6,423,085 B1 | 7/2002 | Murayama et al. |
| 6,428,489 B1 | 8/2002 | Jacobsen et al. |
| 6,440,088 B1 | 8/2002 | Jacobsen et al. |
| 6,468,266 B1 | 10/2002 | Bashiri et al. |
| 6,471,673 B1 | 10/2002 | Kastenhofer |
| 6,508,804 B2 | 1/2003 | Sarge et al. |
| 6,553,880 B2 | 4/2003 | Jacobsen et al. |
| 6,575,959 B1 | 6/2003 | Sarge et al. |
| 6,579,246 B2 | 6/2003 | Jacobsen et al. |
| 6,635,069 B1 | 10/2003 | Teoh et al. |
| 6,638,245 B2 | 10/2003 | Miller et al. |
| 6,652,508 B2 | 11/2003 | Griffin et al. |
| 6,656,550 B1 | 12/2003 | Zamore |
| 6,702,782 B2 | 3/2004 | Miller et al. |
| 6,702,802 B1 | 3/2004 | Hancock et al. |
| 6,706,025 B2 | 3/2004 | Engelson et al. |
| 6,766,720 B1 | 7/2004 | Jacobsen et al. |
| 6,780,181 B2 | 8/2004 | Kroll et al. |
| 6,835,189 B2 | 12/2004 | Musbach et al. |
| 6,860,893 B2 | 3/2005 | Wallace et al. |
| 6,860,899 B1 | 3/2005 | Rivelli |
| 6,878,151 B2 | 4/2005 | Carrison et al. |
| 6,921,410 B2 | 7/2005 | Porter |
| 6,936,055 B1 | 8/2005 | Ken et al. |
| 6,997,937 B2 | 2/2006 | Jacobsen et al. |
| 7,004,962 B2 | 2/2006 | Stinson |
| 7,037,330 B1 | 5/2006 | Rivelli et al. |
| 7,060,083 B2 | 6/2006 | Gerberding |
| 7,070,607 B2 | 7/2006 | Murayama et al. |
| 7,144,407 B1 | 12/2006 | Lasersohn |
| 7,153,323 B1 | 12/2006 | Teoh et al. |
| 7,166,122 B2 | 1/2007 | Aganon et al. |
| 7,294,137 B2 | 11/2007 | Rivelli et al. |
| 7,332,689 B2 | 2/2008 | Mertens et al. |
| 7,412,285 B2 | 8/2008 | Schroeppel et al. |
| 7,468,070 B2 | 12/2008 | Henry et al. |
| 7,481,800 B2 | 1/2009 | Jacques |
| 7,621,904 B2 | 11/2009 | McFerran et al. |
| 7,645,259 B2 | 1/2010 | Goldman |
| 7,654,979 B2 | 2/2010 | Simpson |
| 7,742,811 B2 | 6/2010 | Schroeppel et al. |
| 7,780,626 B2 | 8/2010 | Wu et al. |
| 7,942,847 B2 | 5/2011 | Stupecky et al. |
| 7,998,165 B2 | 8/2011 | Huffmaster |
| 8,066,667 B2 | 11/2011 | Hayman et al. |
| 8,092,508 B2 | 1/2012 | Leynov et al. |
| 8,202,292 B2 | 6/2012 | Kellett |
| 8,206,373 B2 | 6/2012 | Zhou |
| 8,348,890 B2 | 1/2013 | Gerrans et al. |
| 8,961,550 B2 | 2/2015 | Lenker et al. |
| 9,174,020 B2 | 11/2015 | Allen et al. |
| 9,205,226 B2 | 12/2015 | Allen et al. |
| 9,427,550 B2 | 8/2016 | Dakin et al. |
| 9,550,046 B1 | 1/2017 | Allen |
| 9,555,165 B2 | 1/2017 | Phan |
| 9,844,383 B2 | 12/2017 | Allen |
| 2001/0041862 A1 | 11/2001 | Glickman |
| 2002/0032457 A1 | 3/2002 | Sirhan et al. |
| 2003/0050600 A1 | 3/2003 | Ressemann et al. |
| 2003/0114878 A1 | 6/2003 | Diederich et al. |
| 2003/0199914 A1 | 10/2003 | Diaz |
| 2005/0131453 A1 | 6/2005 | Parodi |
| 2005/0267407 A1 | 12/2005 | Goldman |
| 2006/0106413 A1 | 5/2006 | Bence et al. |
| 2006/0276886 A1 | 12/2006 | George et al. |
| 2007/0088380 A1 | 4/2007 | Hirszowicz et al. |
| 2007/0137651 A1 | 6/2007 | Glassenberg et al. |
| 2008/0045908 A1 | 2/2008 | Gould et al. |
| 2008/0208118 A1 | 8/2008 | Goldman |
| 2008/0262470 A1 | 10/2008 | Lee et al. |
| 2009/0156999 A1* | 6/2009 | Adams ................ A61M 25/005 604/103.09 |
| 2009/0177183 A1 | 7/2009 | Pinkernell et al. |
| 2010/0030200 A1 | 2/2010 | Strauss et al. |
| 2010/0113939 A1 | 5/2010 | Mashimo et al. |
| 2012/0203173 A1 | 8/2012 | Davies et al. |
| 2012/0253447 A1 | 10/2012 | Hayasaka et al. |
| 2013/0131610 A1 | 5/2013 | Dewaele et al. |
| 2014/0163421 A1 | 6/2014 | Van Hoven |
| 2014/0364835 A1* | 12/2014 | Allen .................... A61M 25/10 604/509 |
| 2014/0371709 A1 | 12/2014 | Allen et al. |
| 2014/0371718 A1 | 12/2014 | Alvarez et al. |
| 2015/0351729 A1 | 12/2015 | Chin et al. |
| 2016/0008585 A1 | 1/2016 | Tano |
| 2016/0096002 A1 | 4/2016 | Di Caprio et al. |
| 2016/0158439 A1 | 6/2016 | Allen |
| 2016/0213893 A1 | 7/2016 | Franklin |
| 2017/0049495 A1 | 2/2017 | Yu et al. |

(56) References Cited

U.S. PATENT DOCUMENTS

| | | |
|---|---|---|
| 2017/0095646 A1 | 4/2017 | Norman et al. |
| 2018/0015248 A1 | 1/2018 | Logan et al. |
| 2018/0125502 A1 | 5/2018 | Allen |

FOREIGN PATENT DOCUMENTS

| | | |
|---|---|---|
| CN | 102805893 A | 12/2012 |
| EP | 1131126 B1 | 8/2004 |
| EP | 2389968 A2 | 11/2011 |
| JP | 2003500121 A | 1/2003 |
| WO | WO89/08471 A1 | 9/1989 |
| WO | WO2004/107965 A2 | 12/2004 |
| WO | WO2012/009486 A2 | 1/2012 |
| WO | WO2012/099979 A1 | 7/2012 |
| WO | WO2014/008489 A1 | 1/2014 |

OTHER PUBLICATIONS

Angiodynamics; Soft-vu angiographic catheters; 2 pages; retrieved from the internet (http://www.angiodynamics.com/products/soft-vu) on Aug. 17, 2018.

BMI ESPICOM Pharmaceutical and Medical Device News; Business Monitor Online: Vascular solutions expands complex intervention offerings with turnpike LP catheter; newsleter; 2pages; retrieved from the internet (https://dialog.proquest.com/professional/docview/1753127273?accountid=157282) on Apr. 18, 2018 (Abstract Only).

Cliffton et al.; Technique for visualization and perfusion of bronchial arteries: suggested clinical and diagnostic applications; Cancer; 16; pp. 444-452; Apr. 1963.

Nordson Medical; Extruded tubing technical information; 7 pages; retrieved from the internet (https://www.nordsonmedical.com/Components-and-Technologies/Medical-Tubing/Extruded-Tubing/Technical-Information/) on Aug. 17, 2018.

Rousselot et al.; Selective concentration of anticancer drugs in the liver: Hepatic-artery infusion and induced hepatic outflow block; JAMA; 191(9); pp. 707-710; Mar. 1965.

Vante Plasticweld Systems; Bonds and welds; 13 pages; retrieved from the internet (https://cathetertipping.com/home/our-products/bonding/) on Aug. 17, 2018.

Worldwide Videotex; Angiodynamics PCTA balloon catheter gets FDA market clearance; Biotech Equipment Update 5.9: N/A. Worldwide Videotex; Sep. 1, 1997; 2 pages; retrieved from the internet (https://dialog.proquest.com/professional/docview/680080033?accountid=157282) on Apr. 18, 2018 (Abstract Only).

Zeus; FluoroPEELZ peelable heat shrink; 9 pages; retrieved from the internet (https://www.zeusinc.com/products/heat-shrinkable-tubing/fluoropeelz-peelable-heat-shrink) on Aug. 17, 2018.

Allen et al.; U.S. Appl. No. 15/413,262 entitled "Balloon catheter and methods of fabrication and use," filed Jan. 23, 2017.

Matsuda et al.; Electrospinning fabrication of high-trackable catheter tip with gradually graded or gradient flexibility; J. Biomed. Mater. Res. B Appl. Biomater.; 1(35); pp. 35-41 doi: 10.1002/jbm.b.31061; (Abstract Only); Oct. 2008.

* cited by examiner

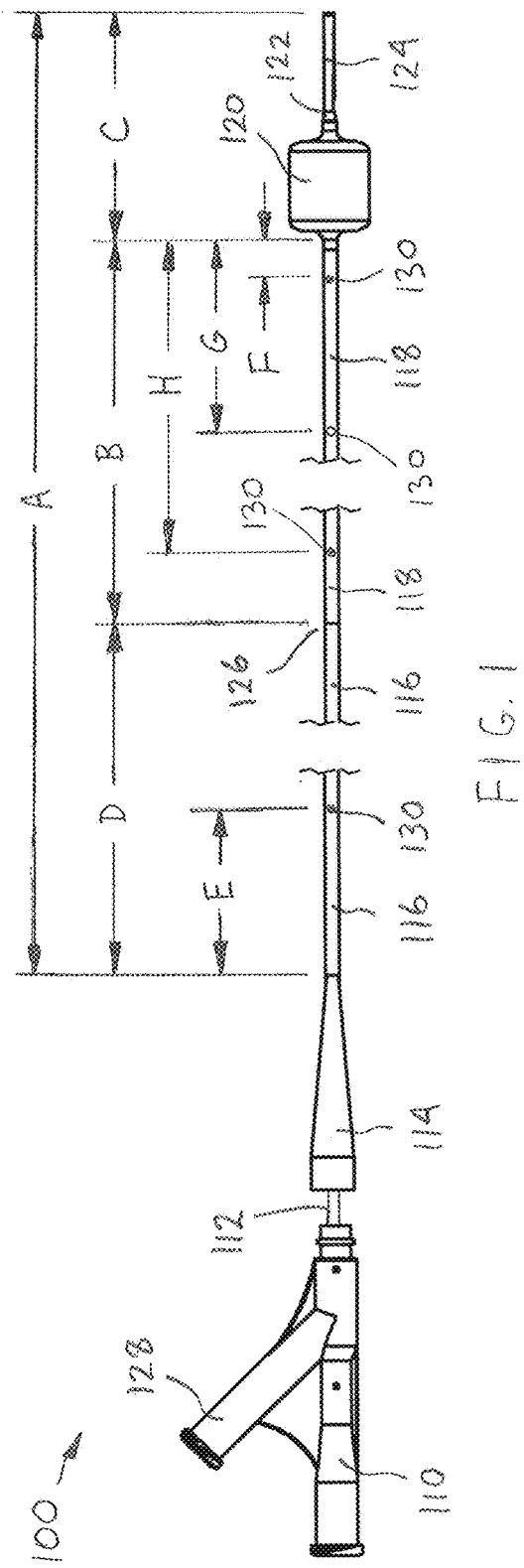
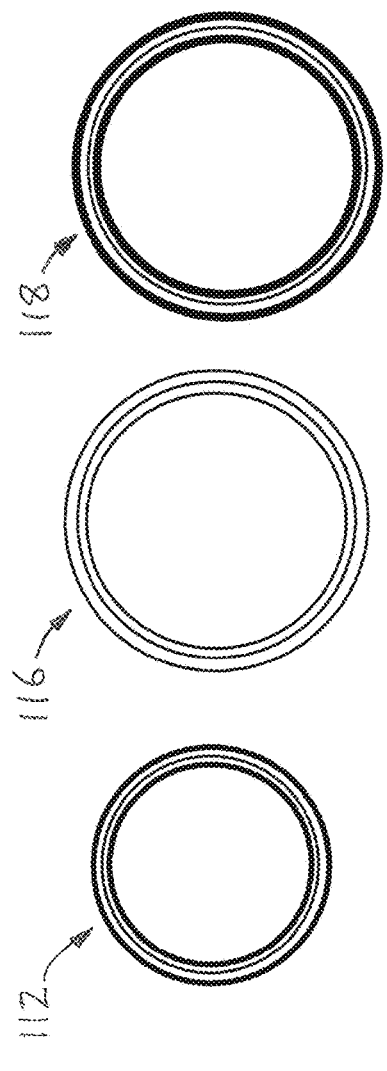
FIG. 1
FIG. 2

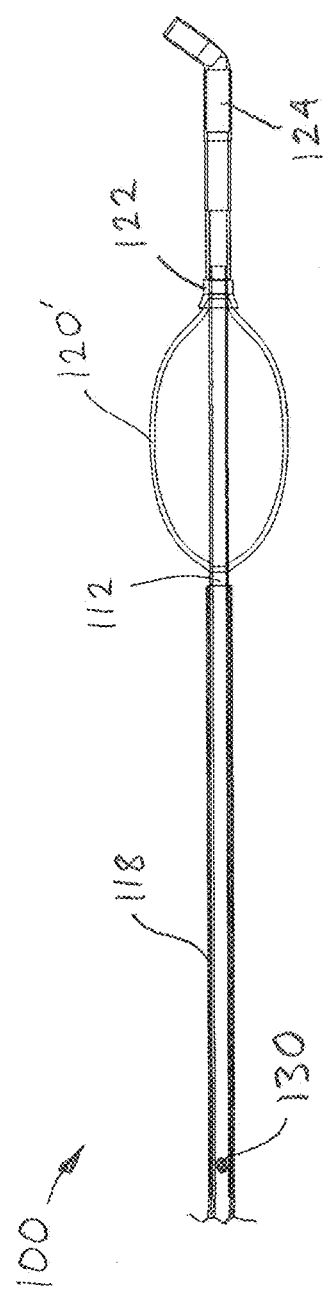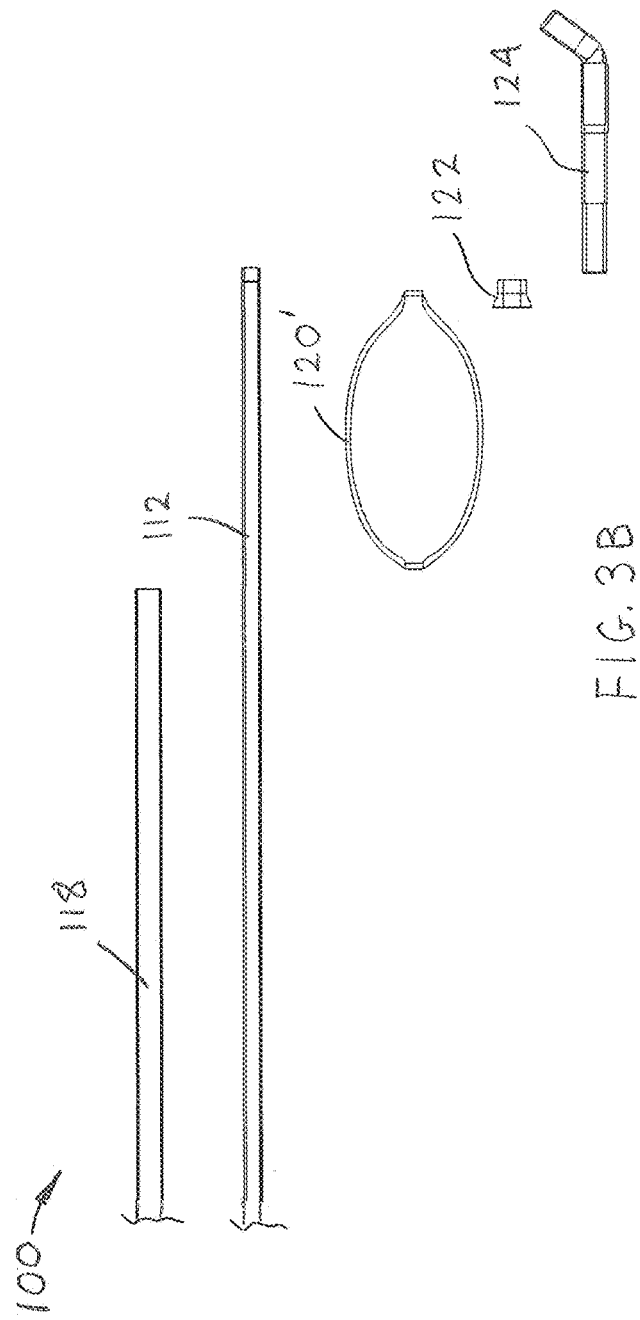
FIG. 3A
FIG. 3B

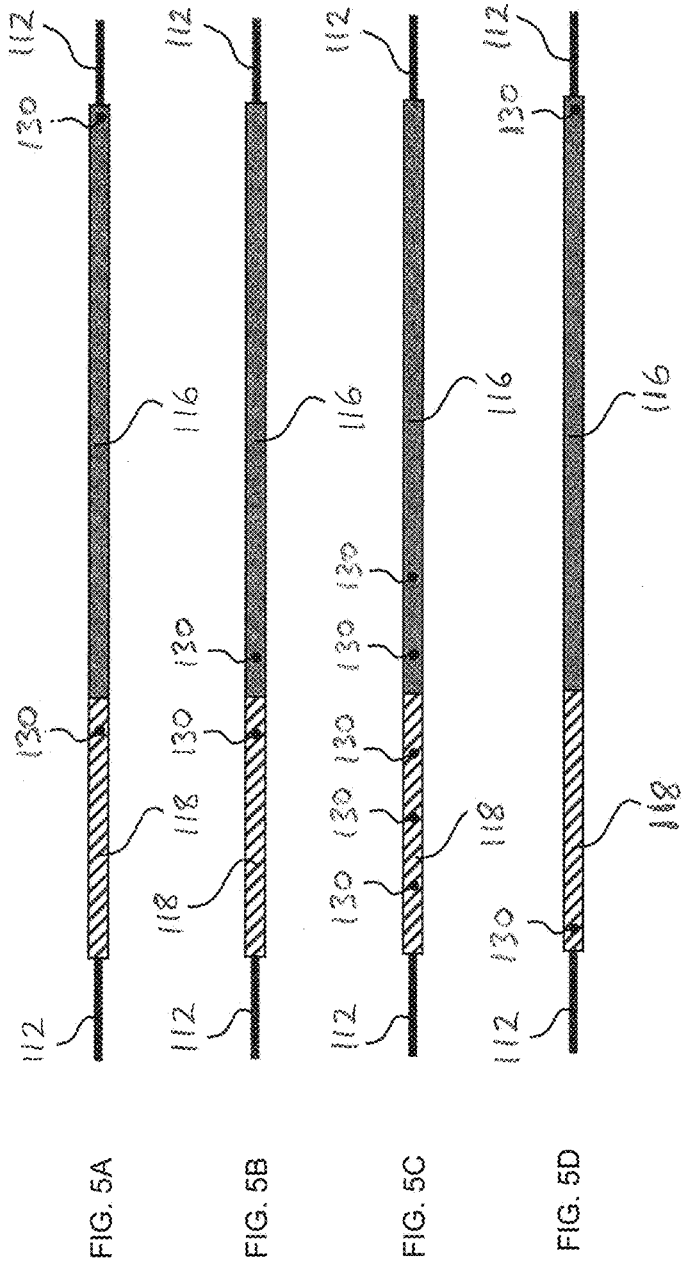
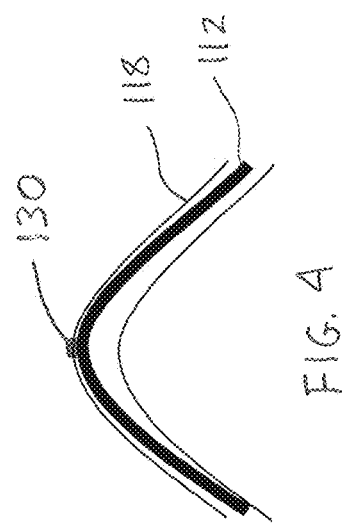

Distal Outer Catheter Section 118

Specimen 1

| Deflection | Test 1 | Test 2 | Test 3 | Avg. |
|---|---|---|---|---|
| 5 mm | 1.8 | 1.5 | 1.6 | 1.6 |
| 10 mm | 2.8 | 3.6 | 3.3 | 3.2 |

Specimen 2

| Deflection | Test 1 | Test 2 | Test 3 | Avg. |
|---|---|---|---|---|
| 5 mm | 2.4 | 2.4 | 2.6 | 2.5 |
| 10 mm | 3.6 | 4.2 | 3.8 | 3.8 |

Specimen 3

| Deflection | Test 1 | Test 2 | Test 3 | Avg. |
|---|---|---|---|---|
| 5 mm | 2.1 | 2.1 | 2.1 | 2.1 |
| 10 mm | 3.4 | 3.3 | 3.2 | 3.3 |

FIG. 7A

Proximal Outer Catheter Section 116

Specimen 1

| Deflection | Test 1 | Test 2 | Test 3 | Avg. |
|---|---|---|---|---|
| 5 mm | 26.1 | 27.37 | 28.46 | 27.3 |
| 10 mm | 38.85 | 42.86 | 42.14 | 41.3 |

Specimen 2

| Deflection | Test 1 | Test 2 | Test 3 | Avg. |
|---|---|---|---|---|
| 5 mm | 27.51 | 18.84 | 18.73 | 21.7 |
| 10 mm | 41.67 | 36.02 | 35.74 | 37.8 |

Specimen 3

| Deflection | Test 1 | Test 2 | Test 3 | Avg. |
|---|---|---|---|---|
| 5 mm | 25.27 | 25.66 | 24.35 | 25.1 |
| 10 mm | 39.98 | 40.12 | 37.71 | 39.3 |

FIG. 7B

HIGH TORQUE CATHETER AND METHODS OF MANUFACTURE

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are devices, systems and methods for effectively transmitting torque from one section to another section of a vascular catheter.

BACKGROUND

Catheters are commonly used in medicine for delivery of fluids, therapeutics and implants as well as in sampling tissues and bodily fluids. Catheters can be constructed with balloons or other tools to dilate tissue, block fluid flow or isolate segments of the anatomy. A relatively common use for a catheter is the delivery of drugs to a target tissue using blood vessels as a means of access. When a balloon is used, the vascular compartment distal to the balloon is isolated from the vascular compartment proximal to the balloon and perfusion of diagnostic, therapeutic or embolic agents is localized and concentrated. Transvascular catheters, especially in the peripheral blood circulation, need to have a small diameter to allow access into small vessels.

One common use for a microcatheter is the delivery of embolic agents and anticancer drugs to a tumor.

According to the NIH, 30,640 people were diagnosed with primary liver cancer (hepatocellular carcinoma, HCC) and 142,820 people were diagnosed with colorectal cancer in the US in 2013. Seventy five percent of these will metastasize to the liver. Liver resection and transplant are the only curative means; however, only small numbers of patients are eligible. Systemic Chemotherapy for primary and metastatic tumors in the liver is ineffective, having a response rate of about 20% and a survival benefit of 10.7 months vs. 7.9 months over symptomatic care.

Trans-Arterial Embolization therapy is the transvascular access for injection of drug and/or embolic agents directly into, or in the vicinity of, the tumor vasculature using a microcatheter. Embolization therapy causes a shutdown of blood flow and, when drug or radioactivity is present, simultaneous release of high concentrations of drug or radioactivity. The technique is also noted for its very low level of toxicity. Chemoembolization was established as a standard of care for intermediate stage hepatocellular carcinoma in 2006. Numerous studies have demonstrated transarterial embolization to be effective on a number of primary cancers and to have better performance than chemotherapy for both HCC and metastatic colorectal cancers in the liver.

Various prior art references provide guidance on aspects of medical catheter construction. For example, U.S. patent application Ser. No. 10/128,977 describes a coaxial catheter whereby a balloon is bonded to an elongated outer tube to prevent the balloon from telescopingly buckling when the balloon is being pushed across a narrow passage. U.S. Pat. No. 6,066,157 describes a coaxial coronary angioplasty catheter whereby an anchor joint is configured to allow distal movement of the inner tube and to prevent proximal movement. U.S. Pat. No. 5,647,198 describes a catheter with a pair of spaced apart balloons that define an intra-balloon space. A lumen passes through the catheter and exits within the intra-balloon space allowing injection of drugs, emulsions, fluids and fluid/solid mixtures. A perfusion lumen or bypass extends from a location proximal to the proximal balloon and to the distal tip to allow shunting of blood past the inflated balloons. U.S. Pat. No. 5,674,198 describes a two balloon catheter that is designed for treating a solid tumor. The balloons are positioned to isolate the blood flow into the tumor and allow injection of a vaso-occlusive collagen material to block the tumor blood supply. Clifton et al. (1963) Cancer 16:444-452 describes a two balloon catheter for the treatment of lung carcinoma. The four lumen catheter includes a lumen for independent injection in the space between the balloons. Rousselot et al. (1965) JAMA 191:707-710 describes a balloon catheter device for delivering anticancer drugs into the liver. See also U.S. Pat. Nos. 6,780,181; 6,835,189; 7,144,407; 7,412,285; 7,481,800; 7,645,259; 7,742,811; U.S. App. No. 2001/008451; U.S. App. No. 2001/0041862; U.S. App. No. 2003/008726; U.S. App. No. 2003/0114878; U.S. App. No. 2005/0267407; U.S. App. No. 2007/0137651; U.S. App. No. 2008/0208118; U.S. App. No. 2009/0182227 and U.S. App. No. 2010/0114021.

Medical catheters often are advanced through torturous vasculature, requiring a flexible distal section that can easily follow the vessel and a stiff proximal section that can support longitudinal advancement of the catheter as it twists and turns through the blood vessels. It is also desirable, in certain applications, that the catheter can transmit torque throughout its length, from the proximal end to the distal tip. This is particularly true when a shaped catheter tip is used. Shaped catheter tips are common and used to direct a guidewire and/or a catheter around acute angles and into branch vessels. A 90-degree shape is among the favored tip configurations. In use, the catheter tip is rotationally oriented so that the angled tip is pointed toward the desired direction of travel. This requires that proximal catheter rotation translates to distal tip rotation.

In general, flexible catheters may track well through turns in the vasculature but cannot transmit torque well, and stiff catheters can transmit torque but cannot track well though torturous vasculature. Accordingly, there is an unmet medical need for a catheter to be both trackable and torqueable.

SUMMARY OF THE DISCLOSURE

In general, in one embodiment, a high torque vascular catheter system includes an inner catheter, a proximal outer catheter section, and a distal outer catheter section. The inner catheter has a proximal portion, a distal portion, and a central lumen extending axially therethrough. The proximal outer catheter section is located over the proximal portion of the inner catheter such that a first generally annular volume remains between an outer diameter of the inner catheter and an inner diameter of the proximal outer catheter section. The distal outer catheter section is located over the distal portion of the inner catheter such that a second generally annular volume remains between the outer diameter of the inner catheter and an inner diameter of the distal outer catheter section. The first and second generally annular volumes are in fluid communication with one another. The distal outer catheter section is more flexible than the proximal outer catheter section. The catheter system further includes at least one discrete connection point connecting the inner catheter to the proximal outer catheter section, and at least one discrete connection point connecting the inner catheter to the distal outer catheter section.

The catheter system may further include a distal tip segment located at the distal portion of the inner catheter. The distal tip segment may be provided with a preset shape that extends a distal end thereof laterally outward. In some embodiments, this preset shape extends the distal end of the distal tip segment through an angle of at least 30 degrees. In some embodiments, the preset shape extends the distal end of the distal tip segment through an angle of about 90 degrees. The catheter system may further include a guidewire configured to be received through the inner catheter and the distal tip segment to guide the distal end of the distal tip segment through torturous vasculature.

In some embodiments, the at least one discrete connection point connecting the inner catheter to the distal outer catheter section has a diameter no greater than 0.006 inches. In some embodiments, the at least one discrete connection point connecting the inner catheter to the distal outer catheter section extends through a circumferential angle no greater than about 30 degrees. The catheter system may include at least three discrete connection points connecting the inner catheter to the distal outer catheter section. In some embodiments not all three discrete connection points are located on the same side of the distal outer catheter section. The discrete connection points may include at least one thermally created spot weld and or at least one drop of hardened glue. In some embodiments, the at least one discrete connection point connecting the inner catheter to the proximal outer catheter section is located on a proximal half of the proximal outer catheter section, and the at least one discrete connection point connecting the inner catheter to the distal outer catheter section is located on a distal half of the distal outer catheter section.

The catheter system may further include an inflatable balloon located on the distal portion of the inner catheter, and the balloon may have an interior in fluid communication with the second generally annular volume of the catheter system. In some embodiments, the inner catheter, the proximal outer catheter section and the distal outer catheter section each contain three coaxial layers. A middle layer of each of the inner catheter, the proximal outer catheter section and the distal outer catheter section may include a stainless steel mesh. In some embodiments, the distal outer catheter section is at least 20 cm long.

In some embodiments, a method of manufacturing a high torque vascular catheter system includes providing an inner catheter having a proximal portion, a distal portion, and a central lumen extending axially therethrough. The method further includes assembling a proximal outer catheter section over the proximal portion of the inner catheter such that a first generally annular volume remains between an outer diameter of the inner catheter and an inner diameter of the proximal outer catheter section. The method further includes assembling a distal outer catheter section over the distal portion of the inner catheter such that a second generally annular volume remains between the outer diameter of the inner catheter and an inner diameter of the distal outer catheter section. In these embodiments, the first and second generally annular volumes are placed in fluid communication with one another, and the distal outer catheter section is more flexible than the proximal outer catheter section. The method further includes forming at least one discrete connection point connecting the inner catheter to the proximal outer catheter section, and forming at least one discrete connection point connecting the inner catheter to the distal outer catheter section.

In some embodiments, the method of manufacturing further includes the step of bending a portion of the catheter system such that a portion of the inner catheter contacts the proximal or distal outer catheter section prior to forming at least one of the discrete connection points at the bend. The step of forming at least one discrete connection point connecting the inner catheter to the distal outer catheter section may include forming a hole in the distal outer catheter section and injecting a fluid into the hole. The step of forming at least one discrete connection point connecting the inner catheter to the distal outer catheter section may include applying thermal energy to a discrete location on the distal outer catheter section sufficient to melt the discrete location.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIG. 1 is a fragmentary side view showing an exemplary high torque vascular catheter system constructed according to aspects of the present disclosure.

FIG. 2 is a cross-sectional view showing lateral cross-sections of an exemplary inner catheter, proximal outer catheter section, and distal outer catheter section.

FIG. 3A is an enlarged side view showing the distal portion of a catheter system similar to the one shown in FIG. 1.

FIG. 3B is an exploded side view showing the distal portion of the catheter system of FIG. 3A.

FIG. 4 is a side cross-sectional view showing a bend in a distal outer catheter section and an inner catheter.

FIGS. 5A-5D are a series of side views showing various exemplary catheters constructed according to aspects of the present disclosure.

FIG. 7A is a chart showing results (in grams) from flexibility testing performed on three sample specimens of an exemplary distal outer catheter section.

FIG. 7B is a chart showing results (in grams) from flexibility testing performed on three sample specimens of an exemplary proximal outer catheter section.

DETAILED DESCRIPTION

Figure 6:
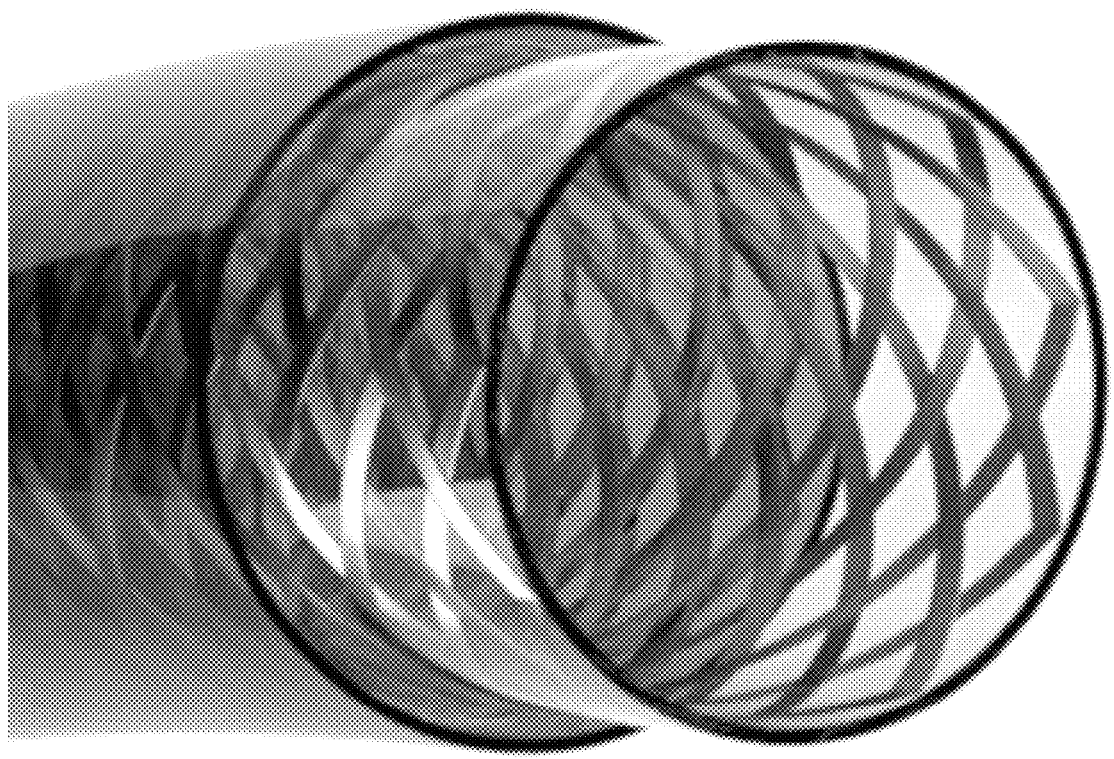
FIG. 6 is an enlarged perspective view showing an inner catheter located inside an outer catheter section in an exemplary embodiment.

Described herein are coaxial catheter designs that allow torque to be effectively transmitted from a relatively stiff catheter section to a relatively flexible catheter section and solve the needs outlined in the Background section above. The disclosed catheters are provided with an outer catheter having at least two sections, including at least one high torque stiff section and one low torque flexible section. The outer catheter is mechanically connected to an inner catheter in at least one discrete connection point on the stiff section and at least one discrete connection point on the flexible section.

As shown in FIG. 1, an exemplary high torque vascular catheter system 100 constructed according to aspects of the present disclosure includes a Y-hub 110, an inner catheter 112, a strain relief 114, a proximal outer catheter section 116, a distal outer catheter section 118, an inflatable balloon 120, a marker band 122, and a distal tip segment 124. Y-hub 110 is shown separated from strain relief 114 for clarity in FIG. 1, but normally is connected thereto. Proximal outer catheter section 116 extends from inside Y-hub 110 to a junction point 126 with distal outer catheter section 118. Distal outer catheter section 118 extends from junction point 126 to the proximal end of balloon 120, and the proximal end of balloon 120 is fluidically sealed with the distal end of the distal outer catheter section 118. Proximal outer catheter section 116 may be joined to distal outer catheter section 118 with a butt joint weld at junction point 126 such that the outer catheter is fluid pressure tight. Inner catheter 112 extends from within Y-hub 110, through proximal outer catheter section 116, distal outer catheter section 118, balloon 120, marker band 122, and into the proximal end of distal tip segment 124. In this exemplary embodiment, the distal end of balloon 120 is fluidically sealed near the distal end of inner catheter 112. With this arrangement, a first generally annular volume (not shown) remains between an outer diameter of the inner catheter 112 and an inner diameter of the proximal outer catheter section 116. Similarly, a second generally annular volume (not shown) remains between the outer diameter of the inner catheter 112 and an inner diameter of the distal outer catheter section 118. These first and second generally annular volumes are in fluid communication with one another at junction point 126. In some embodiments, inner catheter 112 may be generally free to move laterally inside proximal outer catheter section 116 and distal outer catheter section 118. As such, inner catheter 112 may contact these outer catheter sections (as depicted in FIG. 4), and the generally annular volumes may become crescent shaped. What is meant by "generally annular volume" in the claims appended hereto is the space between inner catheter 112 and outer catheter sections 116 and 118, regardless of whether it always has an annular shape.

The first annular volume described above is in fluid communication inside Y-hub 110 with its lateral port 128. The second annular volume is in fluid communication with the interior of balloon 120. Accordingly, when a balloon inflation pressure is provided at lateral port 128, balloon 120 inflates as shown in FIG. 1. When the inflation pressure is removed from lateral port 128, balloon 120 deflates and returns to a retracted state (not shown) surrounding the distal region of inner catheter 112.

In some embodiments, catheter system 100 may have a working length A (i.e. outside of Y-hub 110 and strain relief 114) of about 50 cm to about 150 cm. In some embodiments, the length B of distal outer catheter section 118 is about 30 cm. In some embodiments, the diameter of balloon 120 is about 7 mm, its length is about 8 mm, and the length of distal tip segment 124 is about 8 mm. This results in a combined distance C of balloon and tip of about 1.5 cm, and a total distance B+C distal to junction point 126 of about 31.5 cm. For embodiments having a working length A of 150 cm, this leaves a length D of about 119.5 cm for the portion of proximal outer catheter section 116 that extends from Y-hub 110 and strain relief 114. In some implementations, catheter system 100 is introduced into the target vasculature through a diagnostic catheter (not shown.) In some of these implementations, it is desirable to have about 20 cm of flexible catheter section (e.g. B+C) extending from the diagnostic catheter in order to track through tortuous vasculature. Therefore, with the aforementioned dimensions, junction point 126 and the distal portion of proximal outer catheter section 116 remain inside the diagnostic catheter during a medical procedure.

Referring to FIG. 2, cross-sections of inner catheter 112, proximal outer catheter section 116, and distal outer catheter section 118 are shown. In this exemplary embodiment, each of these three components comprises an inner layer, a middle layer and an outer layer with the following characteristics:

|  | Inner catheter 112 | Proximal outer catheter section 116 | Distal outer catheter section 118 |
| --- | --- | --- | --- |
| Inside diameter (inches) | 0.0200 | 0.0315 | 0.0315 |
| Outside diameter (inches) | 0.0255 | 0.0365 | 0.0370 |
| Inner layer material | PTFE (Teflon) | Polyimide | Polyether block amide (extrusion) |
| Middle layer material | Stainless steel 304 braid; 0.0005" x 0.0025"; 16 wires; 100 PIC | Stainless steel 304 braid; 0.0005" x 0.0025"; 16 wires; 80 PIC | Stainless steel 304 braid; 0.0005" x 0.0025"; 16 wires; 75 PIC |
| Outer layer material | Polyether block amide | Polyimide & Nylon Skim coat | Polyether block amide |
| Other | 900 psi rating | 45 psi rating | 45 psi rating |

Referring to FIGS. 3A and 3B, enlarged views showing the distal portion of catheter system 100 are provided. FIG. 3A shows an assembled view of the distal portion, and FIG. 3B shows an exploded view. Inflated balloon 120' shown in FIGS. 3A and 3B has a more rounded profile than that of balloon 120 shown in FIG. 1. As best seen in FIG. 3A, distal outer catheter section 118 stops just short of the proximal end of balloon 120'. To seal the proximal end of balloon 120' against the distal end of distal outer catheter section 118, a stepped inner sleeve and/or an outer sleeve (neither shown) may be utilized.

As shown in FIGS. 3A and 3B, distal tip segment 124 may be provided with a preset shape that extends a distal end thereof laterally outward. In this embodiment, the distal end extends outward at a 45 degree angle. In other embodiments (not shown), the distal end extends outward at an angle of about 70 to about 90 degrees. In still other embodiments, the tip angle can be between about 10 degrees and about 70 degrees, or between about 90 degrees and about 180 degrees (i.e. the tip can double back on itself.) In some embodiments (not shown), the tip can include two or more bends rather than the single bend of the exemplary embodiment shown. This outward angle allows a medical practitioner to rotate the distal tip segment 124 towards a branch blood vessel (by rotating Y-hub 110 outside of the patient), extend a guidewire (not shown) distally from the distal tip segment 124 into the branch blood vessel, and then track the catheter system 100 over the guidewire into the branch blood vessel. This may be done repeatedly to track the catheter system 100 deep into tortuous vasculature toward target tissue.

As depicted in FIG. 3A, distal outer catheter section 118 may be connected to inner catheter 112 through at least one discrete connection point 130. In some embodiments, discrete connection point(s) 130 may be created by thermal or chemical bonding. For example, laser, radio frequency energy and/or a heated probe such as a soldering iron may be used to melt together the materials of distal outer catheter section 118 and inner catheter 112 to form a tack or spot weld. By way of another example, a hole may be formed in distal outer catheter section 118 and a small amount of glue, adhesive, epoxy or other fluid material may be injected into the hole to bond the two catheters 118 and 112 together. In some embodiments, the resulting discrete connection point 130 described above may have a diameter no greater than 0.006 inches. In some embodiments, the resulting discrete connection point 130 may extend through a circumferential angle no greater than about 30 degrees. In other embodiments (not shown), through pins, wires, micro-rivets, etc. may be used to create the discrete connection points.

As depicted in FIG. 4, when creating a discrete connection point 130, in some embodiments it may be desirable to bend distal outer catheter section 118 and inner catheter 112 so that they make contact with one another. With this approach, a nominal gap of 0.003 inches between inner catheter 112 and distal outer catheter section 118 becomes 0.000 inches on the outside of the bend and 0.006 on the inside of the bend. If a glue or other fluid material is being used to create the discrete connection point 130, the fluid may wick further in the axial direction than in the circumferential direction, creating an oblong discrete connection point 130. In some embodiments, a hole in distal outer catheter section 118 through which the fluid is injected may be no larger than about 0.006. Similar discrete connection points 130 may also be formed between proximal outer catheter 116 and inner catheter 112. The creation of discrete connection points 130 should maintain the patency of the balloon inflation passage between the inner and outer catheters.

Referring to FIGS. 5A-5D, various exemplary catheters constructed according to aspects of the present disclosure are depicted. In these views, the proximal end of the catheter is shown on the right, the distal end is shown on the left, and other components such as a Y-hub, strain relief, balloon, marker band, and distal tip segment (which may or may not be present) are removed for clarity. A sufficient number and placement of discrete connection points 130 should be created to ensure that torque can be adequately transferred from proximal outer catheter 116 to distal outer catheter section 118 through inner catheter 112. However, the number of discrete connection points should be kept to a minimum and their locations chosen so that good flexibility of the catheter is maintained. Each of the exemplary constructs shown in FIGS. 5A-5D is believed to achieve both these goals, as well as other possible constructs. All of the discrete connection points shown in FIGS. 5A-5D are shown on the near side of the catheter for clarity, but in some embodiments they are placed on alternating sides or spaced around the circumference of the catheter so that the catheter is not significantly stiffer along one or two sides.

Referring again to FIG. 1, another exemplary layout of discrete connection points 130 is shown. In this construct, there is one discrete connection point 130 formed between proximal outer catheter 116 and inner catheter 112, and three discrete connection points 130 formed between distal outer catheter section 118 and inner catheter 112. Y-hub 110 may also serve to connect proximal outer catheter 116 and inner catheter 112, but this is not considered a discrete connection point. The discrete connection point 130 formed between proximal outer catheter 116 and inner catheter 112 may be a distance E away from strain relief 114 as shown, which in some embodiments is between about 2 cm and about 10 cm. The three discrete connection points 130 formed between distal outer catheter section 118 and inner catheter 112 may be predetermined distances F, G and H, respectively, away from the proximal end of balloon 120 as shown. In some embodiments, these distances are about 2 cm, about 10 cm, and about 25 cm, respectively. The middle of these three discrete connection points 130 may be located on the opposite side from the other two.

Referring to FIG. 6, an enlarged view showing inner catheter 112 located inside distal outer catheter section 118 is provided. As can be seen, in this exemplary embodiment both inner catheter 122 and distal outer catheter section 118 have internal mesh or braid structures.

In order to be able to track through tortuous vasculature, the distal portion of system 100 should be very flexible. However, very flexible portions of a catheter system tend to transmit torque poorly, as previously mentioned. If a catheter system does not have sufficient torsional rigidity, there is a delay or hysteresis between rotations that are input at the proximal end of the catheter and the desired output rotations that occur at the distal end. In some cases of poor torsional rigidity in the prior art, the proximal end of the catheter may be turned 2, 3 or more rotations for every 1 rotation that occurs at the distal end, with the additional rotations being stored as potential energy in the catheter. These additional rotations may or may not be eventually released, and may release suddenly and unexpectedly. In some implementations of tracking through tortuous vasculature, the proximal end of a prior art catheter may be turned 10 or more times with no rotation occurring at the distal end. With the unique combination of materials, dimensions and discrete connection points 130 disclosed herein, Applicants have found that catheter systems may be constructed that are both highly trackable and torqueable.

Referring to FIGS. 7A and 7B, results from flexibility testing performed on three sample specimens of an exemplary distal outer catheter section 118 (FIG. 7A) and three sample specimens of an exemplary proximal outer catheter section 116 (FIG. 7B) are provided (in grams.) For each of the tests, a 3-point load fixture was used, with one side of the specimen pinned, the other side 5 cm away and resting on the fixture (to alleviate slack), and a force transducer placed in the center of the 5 cm span. The center of each catheter specimen was deflected either 5 mm or 10 mm and a reading from the transducer was recorded (in grams.) Each specimen was tested three times and the results were averaged as shown.

As can be seen by the test results, the distal outer catheter section 118 (FIG. 7A) is significantly more flexible than the proximal outer catheter section 116. In this exemplary embodiment and test set up, the proximal outer catheter sections 116 generally exhibit readings of about 1000% of those for the distal outer catheter sections 118. In other embodiments, the proximal outer catheter sections 116 may generally exhibit readings of about 150%, 200%, 500%, 800% or more compared to those for the distal outer catheter sections 118. Other testing methods may also be used to compare the flexibility of the proximal and distal outer catheter sections.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the disclosure. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the FIGS. is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" or "disclosure" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A high torque vascular catheter system comprising:
    an inner catheter having a proximal portion and a distal portion, the inner catheter having a central lumen extending axially therethrough;
    a proximal outer catheter section located over the proximal portion of the inner catheter such that a first generally annular volume remains between an outer diameter of the inner catheter and an inner diameter of the proximal outer catheter section;
    a distal outer catheter section located over the distal portion of the inner catheter such that a second generally annular volume remains between the outer diameter of the inner catheter and an inner diameter of the distal outer catheter section, the first generally annular volume and the second generally annular volume being in fluid communication with one another, the distal outer catheter section being more flexible than the proximal outer catheter section;
    at least one discrete connection point connecting the inner catheter to the proximal outer catheter section; and
    at least one discrete connection point connecting the inner catheter to the distal outer catheter section,
    wherein the at least one discrete connection point connecting the inner catheter to the distal outer catheter section has a diameter no greater than 0.006 inches.

2. The catheter system of claim 1, further comprising a distal tip segment located at the distal portion of the inner catheter, wherein the distal tip segment is provided with a preset shape that extends a distal end thereof laterally outward.

3. The catheter system of claim 2, wherein the preset shape extends the distal end of the distal tip segment through an angle of at least 30 degrees.

4. The catheter system of claim 2, wherein the preset shape extends the distal end of the distal tip segment through an angle of about 90 degrees.

5. The catheter system of claim 2, further comprising a guidewire configured to be received through the inner catheter and the distal tip segment to guide the distal end of the distal tip segment through torturous vasculature.

6. The catheter system of claim 1, wherein the catheter system comprises at least three discrete connection points connecting the inner catheter to the distal outer catheter section.

7. The catheter system of claim 6, wherein not all three discrete connection points are located on the same side of the distal outer catheter section.

8. The catheter system of claim 1, wherein the discrete connection points comprise at least one thermally created spot weld.

9. The catheter system of claim 1, wherein the discrete connection points comprise at least one drop of hardened glue.

10. The catheter system of claim 1, further comprising an inflatable balloon located on the distal portion of the inner catheter, wherein the balloon has an interior in fluid communication with the second generally annular volume.

11. The catheter system of claim 1, wherein the inner catheter, the proximal outer catheter section and the distal outer catheter section each contain three coaxial layers.

12. The catheter system of claim 11, wherein a middle layer of each of the inner catheter, the proximal outer catheter section and the distal outer catheter section comprises a stainless steel mesh.

13. The catheter system of claim 1, wherein the distal outer catheter section is at least 20 cm long.

14. A high torque vascular catheter system comprising:
    an inner catheter having a proximal portion and a distal portion, the inner catheter having a central lumen extending axially therethrough;
    a proximal outer catheter section located over the proximal portion of the inner catheter such that a first generally annular volume remains between an outer diameter of the inner catheter and an inner diameter of the proximal outer catheter section;
    a distal outer catheter section located over the distal portion of the inner catheter such that a second generally annular volume remains between the outer diameter of the inner catheter and an inner diameter of the distal outer catheter section, the first generally annular volume and the second generally annular volume being in fluid communication with one another, the distal outer catheter section being more flexible than the proximal outer catheter section;
    at least one discrete connection point connecting the inner catheter to the proximal outer catheter section; and
    at least one discrete connection point connecting the inner catheter to the distal outer catheter section,
    wherein the at least one discrete connection point connecting the inner catheter to the distal outer catheter section extends through a circumferential angle no greater than about 30 degrees.

15. A high torque vascular catheter system comprising:
    an inner catheter having a proximal portion and a distal portion, the inner catheter having a central lumen extending axially therethrough;
    a proximal outer catheter section located over the proximal portion of the inner catheter such that a first generally annular volume remains between an outer diameter of the inner catheter and an inner diameter of the proximal outer catheter section;
    a distal outer catheter section located over the distal portion of the inner catheter such that a second generally annular volume remains between the outer diameter of the inner catheter and an inner diameter of the distal outer catheter section, the first generally annular volume and the second generally annular volume being in fluid communication with one another, the distal outer catheter section being more flexible than the proximal outer catheter section;
    at least one discrete connection point connecting the inner catheter to the proximal outer catheter section; and
    at least one discrete connection point connecting the inner catheter to the distal outer catheter section,
    wherein the at least one discrete connection point connecting the inner catheter to the proximal outer catheter section is located on a proximal half of the proximal outer catheter section, and wherein the at least one discrete connection point connecting the inner catheter to the distal outer catheter section is located on a distal half of the distal outer catheter section.

16. A method of manufacturing a high torque vascular catheter system, the method comprising:
   providing an inner catheter having a proximal portion and a distal portion, the inner catheter having a central lumen extending axially therethrough;
   assembling a proximal outer catheter section over the proximal portion of the inner catheter such that a first generally annular volume remains between an outer diameter of the inner catheter and an inner diameter of the proximal outer catheter section;
   assembling a distal outer catheter section over the distal portion of the inner catheter such that a second generally annular volume remains between the outer diameter of the inner catheter and an inner diameter of the distal outer catheter section, wherein the first generally annular volume and the second generally annular volume are placed in fluid communication with one another, wherein the distal outer catheter section is more flexible than the proximal outer catheter section;
   forming at least one discrete connection point connecting the inner catheter to the proximal outer catheter section; and
   forming at least one discrete connection point connecting the inner catheter to the distal outer catheter section,
   further comprising the step of bending a portion of the catheter system such that a portion of the inner catheter contacts the proximal or distal outer catheter section prior to forming at least one of the discrete connection points at the bend.

17. A method of manufacturing a high torque vascular catheter system, the method comprising:
   providing an inner catheter having a proximal portion and a distal portion, the inner catheter having a central lumen extending axially therethrough;
   assembling a proximal outer catheter section over the proximal portion of the inner catheter such that a first generally annular volume remains between an outer diameter of the inner catheter and an inner diameter of the proximal outer catheter section;
   assembling a distal outer catheter section over the distal portion of the inner catheter such that a second generally annular volume remains between the outer diameter of the inner catheter and an inner diameter of the distal outer catheter section, wherein the first generally annular volume and the second generally annular volume are placed in fluid communication with one another, wherein the distal outer catheter section is more flexible than the proximal outer catheter section;
   forming at least one discrete connection point connecting the inner catheter to the proximal outer catheter section; and
   forming at least one discrete connection point connecting the inner catheter to the distal outer catheter section,
   wherein the step of forming at least one discrete connection point connecting the inner catheter to the distal outer catheter section comprises forming a hole in the distal outer catheter section and injecting a fluid into the hole.

18. A method of manufacturing a high torque vascular catheter system, the method comprising:
   providing an inner catheter having a proximal portion and a distal portion, the inner catheter having a central lumen extending axially therethrough;
   assembling a proximal outer catheter section over the proximal portion of the inner catheter such that a first generally annular volume remains between an outer diameter of the inner catheter and an inner diameter of the proximal outer catheter section;
   assembling a distal outer catheter section over the distal portion of the inner catheter such that a second generally annular volume remains between the outer diameter of the inner catheter and an inner diameter of the distal outer catheter section, wherein the first generally annular volume and the second generally annular volume are placed in fluid communication with one another, wherein the distal outer catheter section is more flexible than the proximal outer catheter section;
   forming at least one discrete connection point connecting the inner catheter to the proximal outer catheter section; and
   forming at least one discrete connection point connecting the inner catheter to the distal outer catheter section,
   wherein the step of forming at least one discrete connection point connecting the inner catheter to the distal outer catheter section comprises applying thermal energy to a discrete location on the distal outer catheter section sufficient to melt the discrete location.

* * * * *